United States Patent [19]

Takahara et al.

[11] Patent Number: 4,528,137

[45] Date of Patent: Jul. 9, 1985

[54] PROCESS FOR PREPARING FLUORINE-CONTAINING STEROIDS

[75] Inventors: Takao Takahara, Osaka; Kazuhiro Shimokawa, Suita, both of Japan

[73] Assignee: Daikin Kogyo Co., Ltd., Osaka, Japan

[21] Appl. No.: 569,733

[22] Filed: Jan. 10, 1984

[30] Foreign Application Priority Data

Jan. 12, 1983 [JP] Japan ................................. 58-3064

[51] Int. Cl.$^3$ ................................................ C07J 1/00
[52] U.S. Cl. ............................. 260/397.4; 260/397.5; 260/397.45
[58] Field of Search .................... 260/397.4, 397.45

[56] References Cited

PUBLICATIONS

CA 98(13): 106767u, Article by Lieberman et al., in J. Org. Chem. 48(5) 724–727.
CA 100 (13) Par. 102831X.

*Primary Examiner*—Elbert L. Roberts
*Attorney, Agent, or Firm*—Birch, Stewart, Kolasch & Birch

[57] ABSTRACT

A fluorine-containing 3-oxygenated-$\Delta^{3,5}$-steroid is prepared in a good yield by fluorinating a steroid with a compound of the formula:

RCOOF wherein R is a hydrocarbon group.

12 Claims, No Drawings

PROCESS FOR PREPARING FLUORINE-CONTAINING STEROIDS

The present invention relates to a process for preparing fluorine-containing steroids.

It is known that the introduction of a fluorine atom in a corticosteroid has improved its anti-inflammatory activity.

Hitherto, the fluorine-containing steroids have been prepared by reacting the steroid compounds with a fluorinating agent, by which the alpha- and/or beta-position at the 2, 4, 6, 9, 15 and 16 positions can be fluorinated. Among them, those having 6-alpha- and/or 9-alpha-fluorine have significantly improved anti-inflammatory action. In addition, the steroids in which the A-ring moiety, D-ring moiety and/or a side chain are chemically modified can suppress side effects and have further improved anti-inflammatory effect on rheumatism, etc.

The designation of the positions in the steriod compound is as follows:

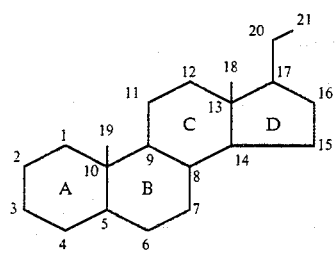

For example, the 6-alpha- or 6-beta-fluoroisomers are shown as follows:

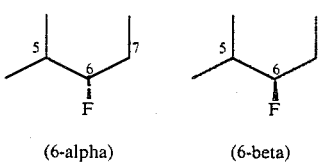

(6-alpha)    (6-beta)

In the conventional processes for fluorinating the steroids, $F_2$, $XeF_2$, $FClO_3$, $CF_3OF$ and $CF_3COOF$ are used as the fluorinating agents. However, none of them can afford the fluorine-containing steroid in a high yield.

Recently, it has been proposed to use $CH_3COOF$ as a fluorinating agent in the fluorination of some organic compounds, and certain aromatic fluorocompounds and fluorocarbohydrates have been prepared:

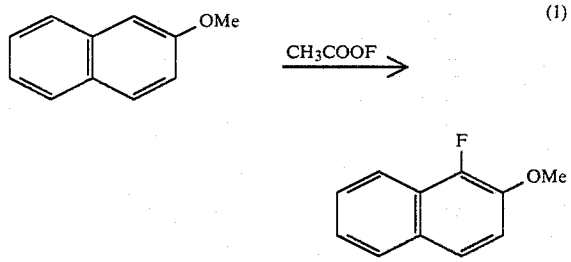

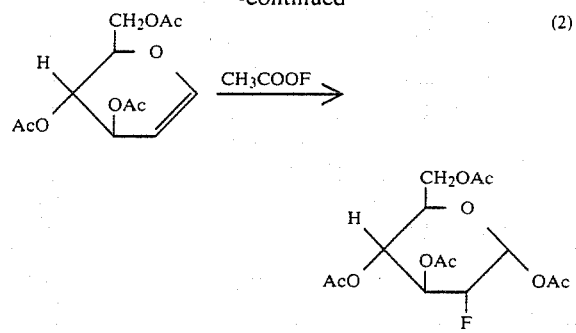

In the former reaction, hydrogen in the aromatic ring is replaced with fluorine, and in the latter reaction, fluorine and the acetoxyl group are added to the double bond.

It has now been found that the fluorination of the steroids with $CH_3COOF$ proceeds in a different reaction mechanism from those described above for the fluorination of the aromatic compounds (1) of the carbohydrates (2), and unexpected fluorine-containing steroids are obtained in good yields.

Accordingly, the present invention provides a process for preparing a fluorine-containing steroid comprising fluorinating a steroid with a compound of the formula: RCOOF wherein R is a hydrocarbon group.

The reaction according to the invention is represented, for example, by the following reaction formula:

$CH_3COOF$ +

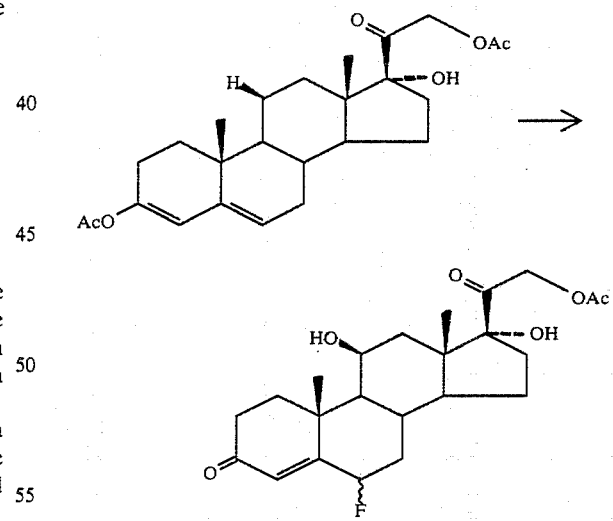

wherein represents a mixture of the alpha-isomer and the beta-isomer.

RCOOF to be used as the fluorinating agent in the invention is prepared by reacting an alkali metal salt of the corresponding carboxylic acid with fluorine gas and the resulting reaction mixture as such is used in the fluorination of the steroid.

The alkali salt of the carboxylic acid may be an alkali metal salt of a lower corboxylic acid, and preferred examples thereof are sodium acetate, sodium propionate and sodium butyrate and corresponding potassium salts.

Fluorine gas is usually diluted to 20% by mole or less with an inert gas such as nitrogen or helium.

The reaction in the process according to the invention is usually carried out in a neutral or slightly acidic solvent which is inert to the reaction. Preferred examples of the solvent are chlorofluorohydrocarbons, organic acids or their mixtures. Any chlorofluorohydrocarbon that is liquid at the reaction temperature is used and their specific examples are $CCl_3F$, $CCl_2F_2$, $CBrF_3$, $CHCl_2F$, $CHClF_2$, $CClF_2CClF_2$, $CBrF_2CBrF_2$, etc. Specific examples of the organic acid are lower carboxylic acids such as acetic acid, propionic acid and butyric acid.

Specific examples of the steroid to be fluorinated by the process according to the invention are as follows:

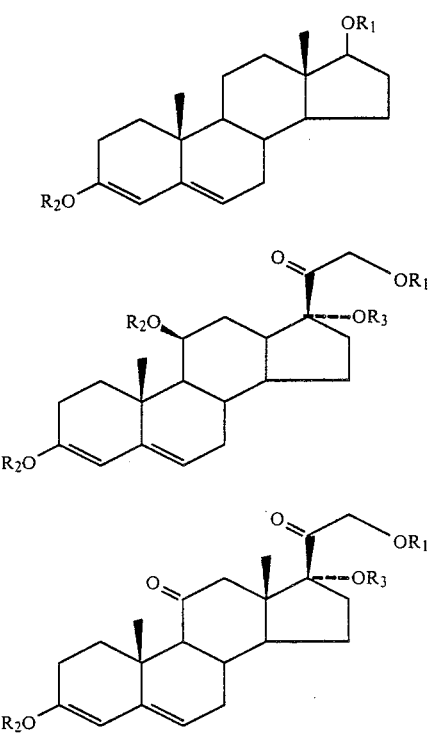

wherein $R_1$, $R_2$ and $R_3$ are each hydrogen or lower acyl such as acetyl, propanoyl, butanoyl, hexanoyl, etc.

If the steroid is hardly soluble in the reaction solvent, it is dissolved in a solvent which is inert to the fluorination of the steroid such as carbon tetrachloride, trichloromethane or dichloromethane, and the resulting solution is employed in the fluorination according to the invention.

The reaction temperature is usually from 30° to −100° C., preferably from 0° to −80° C., more preferably about −75° C.

In the process according to the invention, a mixture of the 6-alpha- and 6-beta-isomers is prepared. Since the 6-beta-isomer has, however, less pharmeceutical effects, it may be converted to the 6-alpha-isomer by dissolving the former in ethyl acetate saturated with dry hydrogen chloride and reacting them for ten hours at room temperature under stirring to obtain the latter (cf. BULLETIN DE LA SOCIETE CHIMIQUE DE FRANCE, 1971, No. 2, 632–638).

The present invention will be hereinafter explained further in detail by the following Examples.

EXAMPLE 1

In a four-necked 200 ml flask, $CCl_3F$ (100 ml), acetic acid (4 ml) and fine powdery sodium acetate (600 mg, 7.3 mmol) were charged and stirred on a dry ice-acetone bath. In the cooled mixture, fluorine gas (12 mmol) diluted to 10% by mole with nitrogen gas was introduced at a rate of 100 ml/min. for 30 minutes. Then, a solution of the steroid (930 mg, 2.5 mmol)) of the formula:

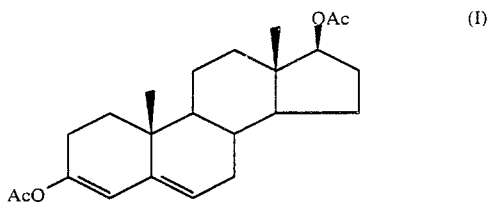

in dichloromethane (10 ml) was added in the flask. The reaction mixture was stirred at −75° C. for ten minutes. Thereafter, a saturated aqueous solution of sodium sulfite (15 ml) was added to stop the reaction and the organic components were extracted with dichloromethane (30 ml×3) and the solvent was evaporated off. The residue was developed on fractionating thin layer chromatography (manufactured by MERCK. Silica gel 60F254, 20 cm×20 cm×2 mm. Solvent: dichloromethane/acetonitrile=9/1 by volume), and a fraction having an Rf of 0.43 was eluted with methanol (50 ml).

The eluted solution was evaporated at room temperature with an evaporator to obtain the solid steroid (531 mg, 1.53 mmol) of the formula:

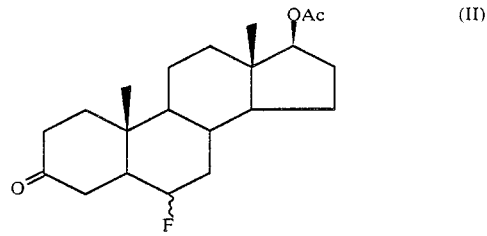

Yield: 61%.

$^1H$—NMR (solvent, $CDCl_3$; internal standard, tetramethylsilane): δ(ppm)=6.1 (br.s, 4—H (6-alpha-isomer)), 5.9 (d, J=4.5 Hz, 4—H (6-beta-isomer)), 5.1 (d, J=48 Hz, 6—H (6-alpha-isomer)), 5.0 (d, J=48 Hz, 6—H (6-beta-isomer)), 4.65 (t, J=8 Hz, 17—H), 2.05 (s, 17—OAc), 1.30 (d, J=1.7 Hz, 10—$CH_3$ (6-beta-isomer)), 1.19 (s, 10—$CH_3$ (6-alpha-isomer)), 0.85 (s, 13—$CH_3$ (6-beta-isomer)) and 0.84 (s, 13—$CH_3$ (6-alpha-isomer)).

$^{19}F$—NMR (solvent, $CDCl_3$; internal standard, benzotrifluoride): δ(ppm)=120.6 (d.m., (6-alpha-isomer)) and 102.8 (t.m., (6-beta-isomer)).

The signal strength in $^{19}F$—NMR shows that the ratio of 6-alpha-isomer to 6-beta-isomer is about 1:2.

EXAMPLE 2

In the same manner as in Example 1 but using, in place of the steroid (I), the steroid (1330 mg, 2.5 mmol) of the formula:

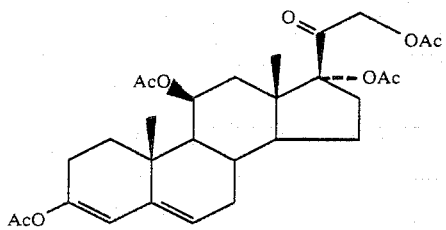

fluorination was carried out to obtain the steroid (630 mg, 1.25 mmol) having an Rf of 0.33 of the formula:

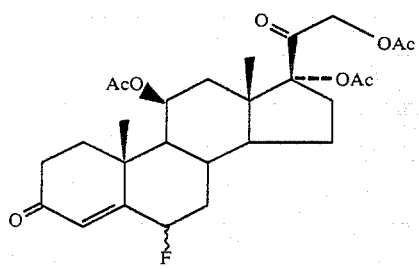

Yield: 50%.

$^1$H—NMR (solvent, CDCl$_3$; internal standard, tetramethylsilane): δ(ppm)=6.0 (br.s, 4—H (6-alpha-isomer)), 5.8 (d, J=4 Hz, 4—H (6-beta-isomer)), 4.8 and 4.6 (d, J=16 Hz, 21—CH$_2$), 2.16, 2.14 and 2.0 (s, 11-, 17- and 21—OAc), 1.34 (d, J=2 Hz, 10—CH$_3$ (6-beta-isomer)), 1.24 (s, 10—CH$_3$ (6-alpha-isomer)), 0.9 (s, 13—CH$_3$ (6-beta-isomer)) and 0.86 (s, 13—CH$_3$ (6-alpha-isomer)).

EXAMPLE 3

In the same manner as in Example 1 but, in place of the steroid (I), using the steroid (1220 mg, 2.5 mmol) of the formula:

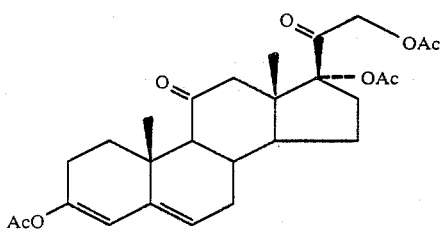

fluorination was carried out to obtain the steroid (947 mg, 2.05 mmol) having an Rf of 0.43 of the formula:

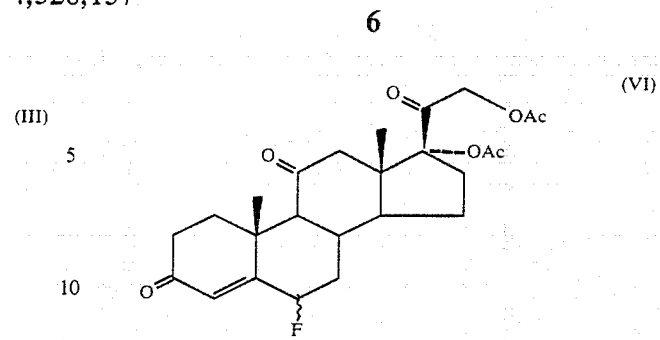

Yield: 82%.

$^1$H—NMR (solvent, CDCl$_3$; internal standard, tetramethylsilane): δ(ppm)=6.04 (br.s, 4—H (6-alpha-isomer)), 5.90 (d, J=4 Hz, 4—H (6-beta-isomer)), 4.80 and 4.68 (d, J=16 Hz, 21—CH$_2$), 2.2 and 2.1 (s, 17- and 21—OAc), 1.50 (br.s, 10—CH$_3$ (6-beta-isomer)), 1.40 (s, 10—CH$_3$ (6-alpha-isomer)), 0.76 (br.s, 13—CH$_3$ (6-beta-isomer)) and 0.72 (s, 13—CH$_3$ (6-alpha-isomer)).

COMPARATIVE EXAMPLE

In the same manner as in Example 1 but using sodium trifluoroacetate (1 g, 7.4 mmol) in place of acetic acid and sodium acetate, the fluorination was carried out to obtain the same fluorine-containing steroid (II) (300 mg, 0.85 mmol) in a lower yield of 34%.

What is claimed is:

1. A process for preparing a 6-fluorosteroid which comprises flourinating a 3-oxygenated-Δ$^{3,5}$-steroid with a compound of the formula:

RCOOF wherein R is a hydrocarbon group.

2. A process according to claim 1, wherein R in the formula is a lower alkyl group.

3. A process according to claim 2, wherein the alkyl group is a methyl, ethyl or propyl group.

4. A process according to claim 1, wherein the compound of the formula:

RCOOF has been prepared by fluorinating an alkali metal salt of the corresponding carboxylic acid with fluorine gas.

5. A process according to claim 1, wherein the fluorination reaction temperature is from 30° to −100° C.

6. A process according to claim 1, wherein the fluorination reaction temperature is from 0° to −80° C.

7. A process according to claim 1, wherein the fluorination reaction is carried out in a solvent.

8. A process according to claim 7, wherein the solvent is a neutral or slightly acidic inert solvent.

9. A process according to claim 8, wherein the solvent is selected from the group consisting of chlorofluorohydrocarbons which are liquid at the reaction temperature, organic acids and mixtures thereof.

10. A process according to claim 9, wherein the chlorofluorohydrocarbon is selected from the group consisting of CCl$_3$F, CCl$_2$F$_2$, CBrF$_3$, CHCl$_2$F, CHClF$_2$, CClF$_2$CClF$_2$ and CBrF$_2$CBrF$_2$.

11. A process according to claim 10, wherein the organic acid is a lower carboxylic acid.

12. A process according to claim 11, wherein the carboxylic acid is selected from the group consisting of acetic acid, propionic acid and butyric acid.

* * * * *